United States Patent [19]
Cosmescu

[11] Patent Number: 5,066,294
[45] Date of Patent: Nov. 19, 1991

[54] PERFORMANCE TESTER APPARATUS FOR A SURGICAL LASER SYSTEM AND METHOD THEREFOR

[76] Inventor: Ioan Cosmescu, 14449 North St., Phoenix, Ariz. 85022

[21] Appl. No.: 527,140
[22] Filed: May 22, 1990
[51] Int. Cl.⁵ .............................................. A61B 17/36
[52] U.S. Cl. ........................................ 606/11; 606/2; 356/138
[58] Field of Search ................... 606/2, 10, 11, 13, 16, 606/17; 128/395–398, 633; 356/138, 150–153

[56] References Cited
U.S. PATENT DOCUMENTS

| | | | |
|---|---|---|---|
| 3,782,832 | 1/1974 | Hackskaylo | 356/153 |
| 4,260,254 | 4/1981 | Braun | 356/153 |
| 4,289,378 | 9/1981 | Remy et al. | 350/174 |

Primary Examiner—Stephen C. Pellegrino
Assistant Examiner—Steven J. Shumaker
Attorney, Agent, or Firm—Harry M. Weiss

[57] ABSTRACT

A performance tester apparatus and method as disclosed for surgical laser system which permits testing of both the laser aiming a laser cutting beams of the surgical laser system. The laser aiming and laser cutting beams are tested for coincidence with each other and a test is made using a bull's eye type configuration on a target to determine the mode and divergence of the laser cutting beam. A single non-inflammable and preferably removable target is used to test both the laser aiming and cutting beams. Suitable shielding means are also used to shield against possible eye injury to an operator or viewer of the test of either or both the laser aiming beam and the laser cutting beam.

14 Claims, 1 Drawing Sheet

PERFORMANCE TESTER APPARATUS FOR A SURGICAL LASER SYSTEM AND METHOD THEREFOR

BACKGROUND OF THE INVENTION

1. Field of the Invention

The invention generally relates to an apparatus and method for testing the performance of a laser system and, in particular, the invention relates to a performance tester apparatus for a surgical laser system and method therefor which is provided with a target that permits checking the forms and accuracy of both a visible laser aiming beam and an invisible laser cutting beam to insure that the axis of the laser cutting beam is accurate and in coincidence with the axis of the laser aiming beam and to further check the size and mode of the laser cutting beam.

2. Description of the Prior Art

Generally, a surgical laser system utilizes a pair of laser beam (i.e. a visible laser aiming beam which is a relatively low energy laser beam provided by a Helium-Neon (HeNe) gas laser and an invisible laser cutting beam which is a relatively high energy laser beam provided by a Carbon Dioxide ($CO_2$) gas laser which in operation are narrowly confined within an articulated arm assembly. A handpiece attached to the end of the arm assembly is manipulated by the surgeon usually at the beginning of a laser type surgical operation to achieve a very accurate or precise focus or to aim the laser cutting beam and thereby point or focus the cutting beam at the proper location within the field of the surgical operation.

Since the laser cutting beam is normally invisible to the human eye, a second laser beam, that is usually called a laser aiming beam, which can be seen because it used a laser light beam that is within the visible spectrum, is used to indicate the exact position of the laser aiming beam by means of a visible dot on the tissue of the surgical patient. When the surgeon has positioned the visible laser aiming beam to be at the desired focus or location, the surgeon then depresses a foot switch associated with the laser surgical system to effectively remove the visible laser aiming beam and activate the laser cutting beam and thereby make incisions for the laser surgical operation.

From this description, it is obvious that the alignment between the laser aiming beam and the laser cutting beam is very critical to the entire laser surgical procedure. The surgeon controlling the laser surgical operation must rely on the fact that the two beams are precisely aligned when an incision is made by the laser cutting beam. Obviously, if the optical systems that are associated with either or both the laser aiming beam or the laser cutting beam are out of alignment with respect to each other, then the focus or location of each of these two laser beams will not be coincident with the focus or location of the other of the two laser beams. Further, the size and mode (shape) of the laser cutting beam is also critical to the incision being made by the surgeon.

In practice, the surgeon previously utilized a combustible material such as a wooden tongue depressor as a target to test the operation and focus of the surgical laser system. The laser aiming beam was directed at the wooden tongue depressor and then the laser cutting beam was activated to determine how accurately the spot burned on the target wooden tongue depressor by the invisible laser cutting beam matches the visible location on the wooden tongue depressor of the visible laser aiming beam. The shape and uniformity of the burned area on the wooden tongue depressor was used to try to indicate whether or not the surgical laser system was functioning properly. However, a burnt area on a wooden target is not always a true indication of the proper or precise focus or size or mode of the laser cutting beam because of the lack of control over how much of the wood is burned or charred by the laser cutting beam or the energy or heat associated therewith.

The problems associated with the above described method previously utilized to try to check for proper orientation and operation of the surgical laser system was that it was very inexact and unreliable and no proper record of the test results was subsequently available to document proper operation of the laser surgical system. The present invention utilizes a more accurate performance tester apparatus for a surgical laser system which includes the use of a removable target located within the test fixture portion of the performance tester apparatus which replaces the handpiece of the laser surgical system to provide a permanent, accurate, and precise record of the proper operation and focus of the laser surgical system. Thus, the precise focus and location of the laser cutting beam with respect to the laser aiming beam can now be permanently recorded thereby insuring the reliability of the laser surgical system as well as a technique to protect the patent, the laser doctor, the surgical center, and the manufacturers of surgical laser systems from accidents due to an improperly aligned surgical laser system.

SUMMARY OF THE INVENTION

One object of the subject invention is to provide an improved performance tester apparatus and method for testing a surgical laser system.

Another object of the subject invention is to provide performance tester apparatus and method for a surgical laser system which permits a viewer to determine the accuracy and coincidence of a laser aiming beam as compared to a laser cutting beam.

Still another object of the subject invention is to provide performance tester apparatus and method for a surgical laser system which checks the alignment of the axis of a laser cutting beam with the axis of a laser aiming beam and also determines the mode of the laser cutting beam.

Another object of the subject invention is to provide performance tester apparatus and method for a surgical laser system which produces a permanent record of the test results of the coincidence of the laser cutting beam and the laser aiming beam, which record may be attached to a patient's records.

A further object of the subject invention is to provide performance apparatus and method for a surgical laser system whereby the propagation mode (shape and intensity cross section) and divergence of the laser cutting beam are tested.

Another object of the subject invention is to provide performance tester apparatus and method for a surgical laser system whereby the operator or viewer is protected for the radiation or energy of the laser cutting and aiming beams.

These and other objects, features and advantages of the present invention, as well as details of the preferred embodiment thereof, will be more fully understood from the following description and drawing.

DESCRIPTION OF THE PREFERRED EMBODIMENTS

In accordance with one embodiment of this invention, a performance tester apparatus is disclosed for a surgical laser system which uses a visible laser aiming beam and an invisible laser cutting beam.

The apparatus comprises target assembly means for attachment at the output of both of the laser beams of the surgical laser system. The target assembly means comprises target means having a target configuration thereon for indicating the precise location of both the visible laser aiming beam and the invisible laser cutting beam to determine if there is coincidence between the visible laser aiming beam and the invisible laser cutting beam as well as to indicate the size and mode of the laser cutting beam.

The apparatus further comprises eye viewing means coupled to the target assembly means for permitting visual observation of the precise location of the visible laser aiming beam on the target configuration of the target means and for permitting visual observation of an impression created on the target configuration of the target means by the invisible laser cutting beam.

In accordance with another embodiment of this invention a method is disclosed for testing a surgical laser system which uses a visible laser aiming beam and an invisible laser cutting beam. The method includes the step of providing a target assembly means for attachment at the output of both of the laser beams of the surgical laser system. The target assembly means comprises target means having a target configuration thereon for indicating the precise location of both the visible laser aiming beam and the invisible laser cutting beam to determine if there is coincidence between the visible laser aiming beam and the invisible laser cutting beam as well as to indicate the size and mode of the laser cutting beam.

The method further includes the step of providing eye viewing means coupled to the target assembly means for permitting visual observation of the precise location of the visible laser aiming beam on the target configuration of the target means and for permitting visual observation of an impression created on the target configuration of the target means by the invisible laser cutting beam.

DESCRIPTION OF THE SPECIFICATION

Figure 1:
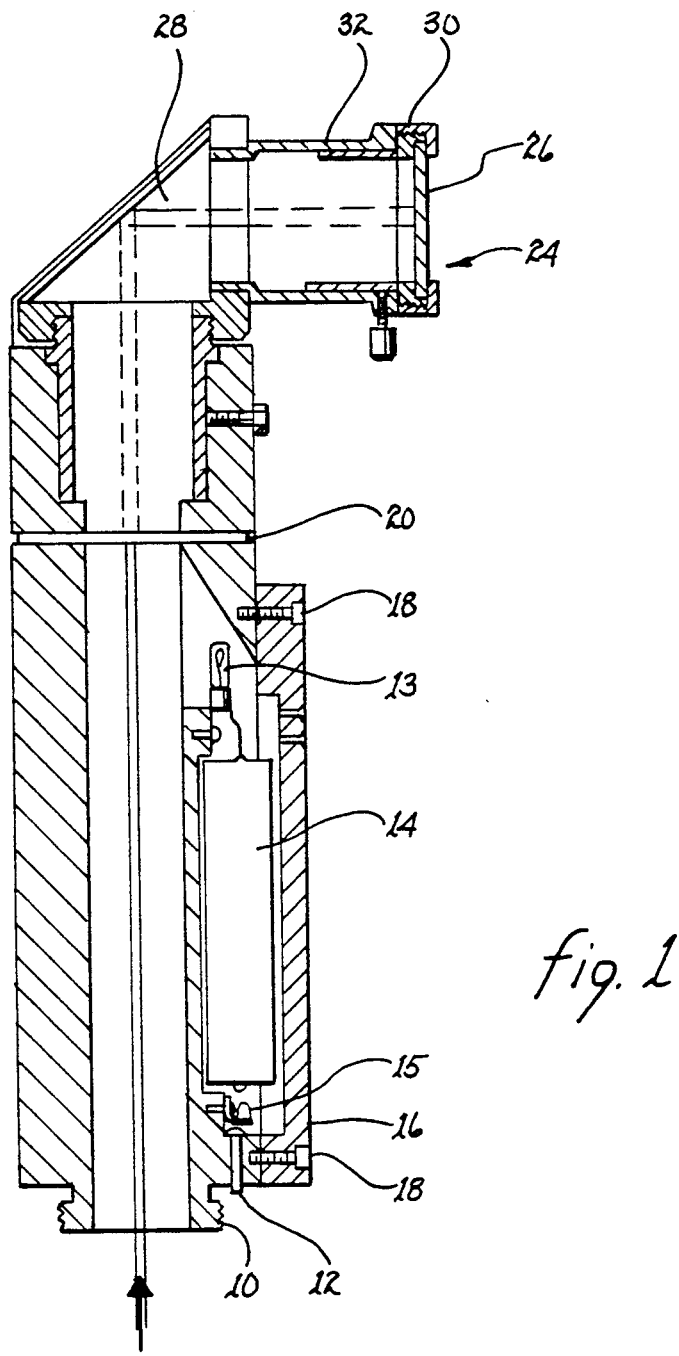
FIG. 1 is a side elevational schematic view of the performance tester apparatus for a surgical laser system in accordance with the preferred embodiment of the present invention.

Referring to FIG. 1, the apparatus of this invention is preferably attached to the laser output portion of a surgical laser system (not shown) by means of a threaded connector portion 10, preferably made of metal. Preferably the entire apparatus is made of aluminum. Pin 12 contacts the mating adjacent surface of the output portion or arm of the surgical laser system as the apparatus is attached and is thereby depressed to turn on light 13. The light 13 is energized by battery 14 and, therefore, the light 13 is caused to be turned on by the pin 12 (in its depressed state) by means of closing an electrical circuit (like the operation of a battery operated flash light) using a switch 15 thus activated by the pin 12.

Figure 2:
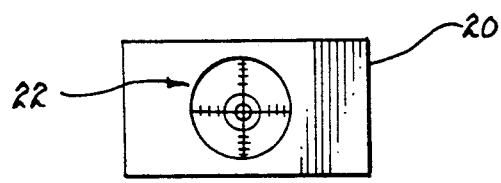
FIG. 2 is a side elevational view of the target used in the apparatus of FIG. 1 which discloses the target's bulls eyes target configuration.

The battery (or if desired several) batteries can be use, are accessible by removing ventilated cover 16. Preferably several (four) screws or bolts 18 are used to hold the cover on the apparatus or to remove it from the apparatus. The apparatus is designed such that, when it is attached to the surgical laser system, it activates the system's interlock which serves to prevent the system's laser cutting beam from being activated until the test is ready to be performed. If desired, the system's laser cutting beam is turned off by a hand or foot switch worked after the apparatus of the subject invention is attached to the surgical laser system. Target 29 (see FIGS. 1 and 2) is manufactured of a non-flammable transparent material which records the burn pattern of the surgical laser system's laser cutting beam or laser and has imprinted thereon a preferably bull's eye type target configuration 22 (with cross hairs having spaced marking thereon) to aid in the critical laser beam alignment procedure. The target 20 is inserted in the space shown in the apparatus of FIG. 1 preferably prior to the attachment of the apparatus to the surgical laser system.

OPERATION

Once the apparatus is attached, the operator or viewer activates the aiming laser beam of the surgical laser system and views the target 20 through eyepiece 24 to establish the location of the laser aiming beam with respect to the bull's eye configuration 22 and the cross hairs thereof. This laser aiming beam test determines whether or not the surgical laser system's laser aiming beam is properly aligned. If the laser aiming beam is located in the center of the cross hairs which would place the beam within the smallest circle of the bull's eye type configuration 22, it is properly aligned. However, if the laser aiming beam is located within the (also sometimes colored red and thereby designated as the smallest red circle) but not centered, the laser surgical system may be used, but the laser aiming beam of the laser surgical system should be aligned in the near future. If the laser aiming beam is located on the edge of the red circle or outside the edge or perimeter of the red circle, the laser surgical system should not be used until an alignment procedure for the laser aiming beam is completed.

The operator or viewer next activates the cutting laser beam of the laser surgical system by means of a hand or a foot switch at a power setting of between 5 and 10 watts. The laser cutting beam will leave an impression on the bull's eye configuration 22 of the target 20 which may be viewed through the eyepiece 24. If the impression form the laser cutting beam is at the same location as the laser aiming beam, the axes of the two beams coincide and the alignment of the system is proper. However is the axes of the two beams do not coincide, the laser surgical system cannot be used.

If the two beams do coincide, the operator or viewer next detaches the apparatus and removes the removable target 20 to determined the propagation mode of the laser cutting beam and the divergence thereof. The preferred mode of the laser cutting beam is $TEM_{00}$. If the beam is too large, then it has a high divergence and cannot be used. The target 20 is preferably stored with patient records to provide a permanent record of the operational test of the surgical laser system.

Both the laser cutting beam which is typically a high energy gas type carbon dioxide laser beam and the laser aiming beam which is typically a low energy, gas type helium neon beam can be harmful to the human eye. For this reason, the apparatus depicted in the preferred embodiment provides means for shielding the operator or viewer from the radiation therefrom in the form of a preferably red filter 26 located int eh eyepiece 24 to shield against the energy of the laser aiming beam and a preferably glass prism 28 which shields against radiation from the laser cutting beam. A threaded coupling assembly 30 is used to attach or detach the red filter 26 to the apparatus. Conduit 32 connects the eyepiece 24 to the portion of the apparatus containing the glass prism 28.

While the invention has been particularly shown and described with reference to a preferred embodiment thereof, it will be understood by those skilled int eh art that changes in form and detail may be made therein without departing from the spirit and the scope of the invention. For example, if desired, a video type recorder can be used by connection to the eyepiece 24 of the apparatus. Accordingly, the term eye viewing means that is used in the attached patent claims is intended to cover or define both visual observation of the tests performed by the apparatus or video or other recording of these tests.

I claim:

1. An apparatus for testing the performance of a visible laser aiming beam and invisible laser cutting beam output of a surgical laser system comprising, in combination:
   target assembly means for attachment to said visible and invisible beam output;
   target means removably coupled to said target assembly means for measuring the performance attributes of said visible and invisible beam output, said target means further comprises target configuration means for indicating a precise location of impingement of said visible and invisible beam output on said target means;
   light means coupled to said target assembly means for providing a source of light within said target assembly means to illuminate said location; and
   eye viewing means coupled to said target assembly means for permitting visual observation of said location of said visible and invisible beam output; said target configuration means comprises a calibrated target to permit evaluation of the transverse electromagnetic mode and beam diameter of said invisible laser cutting beam and the location of said invisible laser cutting beam with respect to said visible laser aiming beam.

2. The apparatus of claim 1 further comprising switch means for actuating said light means to illuminate said location.

3. The apparatus of claim 1 wherein said eye viewing means further comprises preventing means located in a potential accidental beam path of said output for preventing both said invisible laser cutting beam and said visible laser viewing beam from making direct contact with a viewer's eye.

4. The apparatus of claim 3 wherein said means for preventing comprises glass prism means for preventing said invisible laser cutting beam from making direct contact with a viewer's eye and filter means for preventing said visible laser viewing beam from making direct contact with a viewer's eye.

5. The apparatus of claim 4 wherein said filter means is a red absorbing filter.

6. The apparatus of claim 1 wherein said target configuration means comprises a bull's eye target adapted to evaluate the performance of an invisible laser cutting beam which is a carbon Dioxide laser beam.

7. The apparatus of claim 1 wherein said target configuration means comprises a bull's eye target adapted to evaluate the performance of a visible laser aiming beam which is a Carbon Dioxide laser beam.

8. A method for testing the performance of a visible laser aiming beam and invisible laser cutting beam output of a surgical laser system comprising the steps of:
   providing target assembly means for attachment to said visible and invisible beam output;
   providing target means removably coupled to said target assembly means for measuring the performance attributes of said visible and invisible beam output, wherein said step of providing target means further comprises the step of providing a target configuration for indicating a precise location of impingement of said visible and invisible beam output on said target means;
   providing light means coupled to said target assembly means for providing a source of light within said target assembly means to illuminate said location; and
   providing eye viewing means coupled to said target assembly means for permitting visual observation of said location of said visible and invisible beam output; said target configuration comprises a calibrated target to permit evaluation of the transverse electromagnetic mode and beam diameter of said invisible laser cutting and the location of said invisible laser cutting beam with respect to said visible laser aiming beam.

9. The method of claim 8 further comprising the step of providing switch means for actuating said light means to illuminate said location.

10. The method of claim 8 wherein said step of providing said eye viewing means further comprises the step of providing preventing means located in a potential accidental beam path of said output for preventing both said invisible laser cutting beam and said visible laser viewing beam from making direct contact with a viewer's eye.

11. The method of claim 10 wherein said step of providing preventing means comprises the step of providing glass prism means for preventing said invisible laser cutting beam from making direct contact with a viewer's eye and providing filter means for preventing said visible laser viewing beam from making direct contact with a viewer's eye.

12. The method of claim 11 wherein said step of providing filter means is the step of providing a red absorbing filter.

13. The method of claim 8 wherein said target configuration is bull's eye target adapted to evaluate the performance of an invisible laser cutting beam which is a Carbon Dioxide laser beam.

14. The method of claim 8 wherein said target configuration is a bull's eye target adapted to evaluate the performance of a visible laser aiming beam which is a Helium Neon laser beam.

* * * * *

UNITED STATES PATENT AND TRADEMARK OFFICE
CERTIFICATE OF CORRECTION

PATENT NO. : 5,066,294

DATED : 11/19/91

INVENTOR(S) : IOAN COSMESCU

It is certified that error appears in the above-identified patent and that said Letters Patent is hereby corrected as shown below:

COLUMN 6, line 12, (claim 7), delete "Carbon Dioxide" and substitute therefore -- Helium Neon--.

Signed and Sealed this

Ninth Day of March, 1993

Attest:

STEPHEN G. KUNIN

Attesting Officer

Acting Commissioner of Patents and Trademarks